United States Patent
Leysieffer et al.

(10) Patent No.: US 6,537,200 B2
(45) Date of Patent: Mar. 25, 2003

(54) PARTIALLY OR FULLY IMPLANTABLE HEARING SYSTEM

(75) Inventors: Hans Leysieffer, Taufkirchen (DE); Günter Rinser, Feldkirchen (DE)

(73) Assignee: Cochlear Limited, Lane Cove (AU)

( * ) Notice: Subject to any disclaimer, the term of this patent is extended or adjusted under 35 U.S.C. 154(b) by 162 days.

(21) Appl. No.: 09/818,763

(22) Filed: Mar. 28, 2001

(65) Prior Publication Data
US 2002/0071581 A1 Jun. 13, 2002

(30) Foreign Application Priority Data
Mar. 28, 2000 (DE) ......................... 100 15 421

(51) Int. Cl.$^7$ ............................................. H04R 25/00
(52) U.S. Cl. ........................................... 600/25; 381/312
(58) Field of Search ..................... 600/25; 381/312, 381/315

(56) References Cited

U.S. PATENT DOCUMENTS

| | | |
|---|---|---|
| 3,557,775 A | 1/1971 | Mahoney |
| 3,712,962 A | 1/1973 | Epley |
| 3,764,748 A | 10/1973 | Branch et al. |
| 4,352,960 A | 10/1982 | Dormer et al. |
| 4,441,210 A | 4/1984 | Hochmair et al. |
| 4,729,366 A | 3/1988 | Schaefer |
| 4,850,962 A | 7/1989 | Schaefer |
| 4,932,405 A * | 6/1990 | Peeters et al. ............. 607/57 |
| 4,988,333 A | 1/1991 | Engebretson |
| 5,015,224 A | 5/1991 | Maniglia |
| 5,015,225 A | 5/1991 | Hough et al. |
| 5,070,535 A | 12/1991 | Hochmair et al. |
| 5,095,904 A | 3/1992 | Seligman et al. |
| 5,271,397 A | 12/1993 | Seligman et al. |
| 5,277,694 A | 1/1994 | Leysieffer et al. |
| 5,279,292 A | 1/1994 | Baumann et al. |

(List continued on next page.)

FOREIGN PATENT DOCUMENTS

| | | | |
|---|---|---|---|
| DE | 3625891 | * | 2/1988 |
| EP | 0 190 836 | | 8/1986 |
| EP | 0 200 321 | | 11/1986 |
| EP | 0 263 254 | | 4/1988 |
| EP | 0 671 818 | | 9/1995 |
| EP | 0 823 188 | | 4/1996 |
| WO | 97/18689 | | 5/1997 |
| WO | 98/03035 | | 1/1998 |
| WO | 98/06237 | | 2/1998 |
| WO | 98/36711 | | 8/1998 |
| WO | 98/51124 | | 11/1998 |
| WO | 99/07436 | | 2/1999 |
| WO | 99/08475 | | 2/1999 |
| WO | 99/08481 | | 2/1999 |

OTHER PUBLICATIONS

Suzuki et al., "Implantation of Partially Implantable Middle Ear Implant and the Indication", pp. 160–169, 1988, Advances in Audiology, vol. 4.

(List continued on next page.)

Primary Examiner—John A. Jeffery
(74) Attorney, Agent, or Firm—Nixon Peabody LLP; David S. Safran

(57) ABSTRACT

The invention relates to a partially or fully implantable hearing system which is provided with a unit (14, 30; 460) for electromechanical or electroacoustic stimulation of the middle ear or inner ear or direct electrical stimulation of the inner ear. The hearing system furthermore comprises means (26, 126, 154, 526) for direct linkage of the hearing system to telecommunication networks without using telecommunication terminal devices.

36 Claims, 11 Drawing Sheets

U.S. PATENT DOCUMENTS

| | | |
|---|---|---|
| 5,411,467 A | 5/1995 | Hortmann et al. |
| 5,597,380 A | 1/1997 | McDermott et al. |
| 5,601,617 A | 2/1997 | Loeb et al. |
| 5,603,726 A | 2/1997 | Schulman et al. |
| 5,626,629 A | 5/1997 | Faltys et al. |
| 5,734,976 A * | 3/1998 | Bartschi et al. .............. 381/328 |
| 5,814,095 A | 9/1998 | Müller et al. |
| 5,824,022 A | 10/1998 | Zilberman et al. |
| 5,859,916 A | 1/1999 | Ball et al. |
| 5,941,814 A | 8/1999 | Lehner et al. |
| 5,999,632 A | 12/1999 | Leysieffer et al. |
| 6,021,207 A | 2/2000 | Puthuff et al. |
| 6,094,492 A * | 7/2000 | Boesen ....................... 381/312 |
| 6,123,660 A | 9/2000 | Leysieffer |
| 6,154,677 A | 11/2000 | Leysieffer |
| 6,162,169 A | 12/2000 | Leysieffer |
| 6,198,971 B1 | 3/2001 | Leysieffer |
| 6,227,204 B1 | 5/2001 | Baumann et al. |
| 2001/0047193 A1 * | 11/2001 | Zierhofer et al. .............. 607/57 |
| 2002/0044669 A1 * | 4/2002 | Meyer et al. ................ 381/312 |

OTHER PUBLICATIONS

Leysieffer et al., Ein vollständig implantierbares Hörsystem für Innenohrschwerhörige: TICA LZ 3001 (ATotally Implantable Hearing Device for the Treatment of Sensorineural Hearing), pp. 853–863, 1998, HNO vol. 46.

Yanagihara et al., "Implantable Hearing Aid", pp. 869–872, Aug. 1997, Arch Otolaryngol Head Neck Surgery, vol. 113.

Zenner et al., "Erste Implantation eines vollständig implantierbaren elektronischen Hösystems bei Patienten mit Innenohrschwerhörigkeit", pp. 844–852, 1998, HNO.

* cited by examiner

PARTIALLY OR FULLY IMPLANTABLE HEARING SYSTEM

BACKGROUND OF THE INVENTION

1. Field of the Invention

This invention relates to a partially or fully implantable hearing system which is provided with a unit for electromechanical or electroacoustic stimulation of the middle ear or inner ear or direct electrical stimulation of the inner ear.

2. Description of Related Art

Here, a "hearing disorder" is defined as inner ear damage, middle ear damage, combined inner ear and middle ear damage, cochlear deafness which necessitates the use of a cochlear implant, as well as retrocochlear hearing disorders which necessitate the use of a brain stem implant, i.e. in brief, everything which prevents or adversely affects sound pick-up and/or routing to the brain stem.

In recent years, rehabilitation of sensorineural hearing disorders with partially implantable electronic systems has acquired major importance. This applies especially to the group of patients in which hearing has completely failed due to accident, illness or other effects or the group of patients in which hearing has not been functional since birth. If, in these cases, only the inner ear (cochlea) and not the central neural auditory path is affected, electrical signals stimulate the remaining auditory nerve and thus produce a hearing impression which can lead to speech comprehension. In these so-called cochlear implants, an array of stimulating electrodes are inserted into the cochlea and controlled by an electronic system; this hermetically tight and biocompatibly encapsulated electronic module being surgically embedded in the bony area behind the ear (mastoid). The electronic system, however, contains essentially only decoder and driver circuits for the stimulating electrodes. Acoustic sound reception, conversion of this acoustic signal into electrical signals and their further processing, take place basically externally in a so-called speech processor which is worn outside on the body. The speech processor converts the preprocessed signals into a radio frequency carrier signal which is correspondingly coded and transmitted to the implant via inductive coupling through the closed skin (transcutaneously). The sound-receiving microphone is located exclusively outside the body and, in most applications, in a housing of a behind-the-ear hearing aid worn on the external ear. The microphone is connected by a cable to the speech processor. Such cochlear implant systems, their components, and the principles of transcutaneous signal transmission are described, for example, published European Patent Application in EP-A-0 200 321 and in U.S. Pat. Nos. 5,070,535, 4,441,210, and 5,626,629. Processes of speech processing and speech coding in cochlear implants are described, for example, in published European Patent Applications EP-A-0 823 188 and EP-B-0 190 836, and in U.S. Pat. Nos. 5,597,380, 5,271,397, 5,095,904, 5,601,617 and 5,603,726.

In addition to rehabilitation of congenitally deaf persons and those who have lost their hearing using cochlear implants, for some time there have been approaches which offer improved rehabilitation to patients with a sensorineural hearing disorder which cannot be surgically corrected with partially or fully implantable hearing aids or with conventional hearing aids. The principle consists in most embodiments in stimulating an ossicle of the middle ear or the inner ear directly via mechanical or hydromechanical stimulation and not via the amplified acoustic signal of a conventional hearing aid, in which the amplified acoustic signal is supplied to the external auditory canal. The actuator stimulus of these electromechanical systems is accomplished with different physical transducer principles, for example, by electromagnetic and piezoelectric systems. The advantage of these processes is realized mainly in improved tone quality compared to conventional hearing aids and for fully implanted systems in the fact that the hearing prosthesis is not visible. Such partially or fully implantable electromechanical hearing aids are described for example by Yanigahara, et al., in Arch. Otolaryngol. Head Neck Surg, Vol. 113, August 1987, pp. 869–872; Suzuki, et al., in Advances in Audiology, Vol. 4, Karger Basel, 1988; Leysieffer, et al., in HNO, Vol. 46, 1998, pp. 853–863; Zenner, et al., in HNO, Vol. 46, 1998, pp. 844–852, and in numerous patent documents, especially in U.S. Pat. Nos. 5,999,632, 5,277,694, 5,411,467, 3,764,748, 4,352,960, 5,015,224, 5,015,225, 3,557,775, 3,712,962, 4,729,366, 4,988,333, 5,814,095, 4,850,962, 5,859,916, in published European Patent Application EP-B-0 263 254, and published International Patent Applications WO-A-98/36711, WO-A-98/06237, WO-A-98/03035, WO-A-99/08481, WO-A-99/08475, WO-A-99/07436, and WO-A-97/18689.

In all the aforementioned rehabilitation devices, it now seems highly sensible to design the systems such that they can be fully implanted. Depending on the desired function, such hearing systems consist of three or four functional units: (1) a sensor (microphone) which converts the incident airborne sound into an electrical signal, (2) an electronic signal processing, amplifying, and implant control unit, (3) an electromechanical or implantable electroacoustic transducer which converts the amplified and preprocessed sensor signals into mechanical or acoustic vibrations and supplies them via suitable coupling mechanisms to the damaged middle and/or inner ear or a cochlear stimulating electrode in cochlear implants, and (4) an electrical power supply system which supplies the aforementioned modules. Furthermore, there can be an external unit which makes electrical recharging energy available to the implant when the implant-side power supply unit contains a rechargeable secondary battery. Especially advantageous devices and processes for charging of rechargeable implant batteries are described in commonly owned, co-pending U.S. patent application Ser. No. 09/311,566 which is hereby incorporated by reference, and in U.S. Pat. No. 5,279,292. Preferably, there can also be a telemetry unit with which patient-specific audiologic data can be transmitted wirelessly in both directions or programmed in the implant and thus permanently stored, as was described in Leysieffer, et al., in HNO, Vol. 46, 1998, pp. 853–863.

To enable simple updating of the operating software of the implant without surgery, in commonly owned, co-pending U.S. patent application Ser. No. 09/369,182 which is hereby incorporated by reference, it is proposed that the implant electronics be made such that at least parts of the operating program can be altered or replaced by data transmitted from an external unit via a telemetry means which preferably works inductively.

One aspect in hearing systems is their use in conjunction with telecommunication means.

Published International Application WO 98/51124 relates to matching of telecommunication terminal devices such as the mobile part of a cordless phone to hearing systems for rehabilitation of hearing disorders. Here, it has been proposed that the mobile part be equipped with a unit which converts the signal delivered to the speaker of the mobile part, depending on information regarding the hearing system used by the user compared to normal operation for individuals with intact hearing, such that the user of the hearing system acquires a hearing impression as optimum as possible. The hearing aids are conventional electroacoustic devices or a cochlear implant in which the microphone and the speech processor are worn externally behind the external ear. In the latter case, it is proposed that the signal, which is conditioned by the telecommunication terminal device especially for the hearing aid used, be supplied directly to the receiver of the cochlear implant or the implanted electrode wire. For the latter case, the use of a socket or a corresponding bus is being proposed. The disadvantage in this hearing system is that specially modified telecommunication terminal devices must be used to enable the hearing system user to use the telecommunication networks.

U.S. Pat. No. 5,824,022 discloses a cochlear implant system which has an implantable cochlea stimulator and a speech processor unit which is worn behind the ear and which, on the one hand, processes the acoustic signals which are captured via a microphone and transmits them inductively to the implantable cochlea stimulator and, on the other hand, via a radio frequency route can communicate bidirectionally with a remote control which has an audio socket for receiving radio, TV and Walkman audio signals which can be processed by means of an audio processor and can be sent to the speech processor unit.

U.S. Pat. No. 6,021,207 discloses an insert earphone which can be inserted into the auditory canal and which has a microphone and a speaker. The insert earphone is in wireless bidirectional communication with a remote control unit in order to send, on the one hand, the audio signals acquired by the microphone to it and, on the other hand, to receive audio signals from it and output them via the speaker. The remote control can be a mobile phone or a unit connected to it.

Published European Patent Application EP 0 671 818 A1 discloses an RF receiver which, including the battery and earphone, can be arranged in a housing which can be inserted into the auditory canal of an individual.

SUMMARY OF THE INVENTION

A primary object of this invention is to devise a partially or fully implantable hearing system which enables its user to easily use telecommunication networks.

This object is achieved in conformity with the invention by a partially or fully implantable hearing system which is directly linkable to telecommunication networks without terminals. In this approach in accordance with the invention, it is advantageous that the hearing system is not linked via the telecommunication terminal devices but that linkage is achieved by a modification of the hearing system itself. Hearing systems linked via the telecommunication terminal devices must be either tuned in a complex manner specially to the hearing system which is being used, or, if this tuning is omitted due to the then absence of tuning between the hearing system and the telecommunication terminal device, such systems allow only poor hearing quality. Furthermore, by modification of the hearing system itself, the use of a telecommunication terminal device in fact is omitted. This entails a major facilitation for the user of the hearing system since he no longer needs to carry this terminal device and thus, for example, has his hands free at all times. In this way, voice messages can also be received in a manner not visible to third parties and particularly inaudibly so that third parties are not disturbed. The acoustic pick-up and the stimulation unit of the hearing system thus functionally replace the corresponding components (microphone and earphone) of a telecommunication terminal device.

Basically the hearing system can also be designed for rehabilitation of a hearing disorder of the user or also for a user without a hearing disorder. In the latter case, an "invisible mobile phone" can be implemented when the system is fully implanted.

These and further objects, features and advantages of the present invention will become apparent from the following description when taken in connection with the accompanying drawing which, for purposes of illustration only, shows several embodiments in accordance with the present invention.

DETAILED DESCRIPTION OF THE INVENTION

Figure 1:
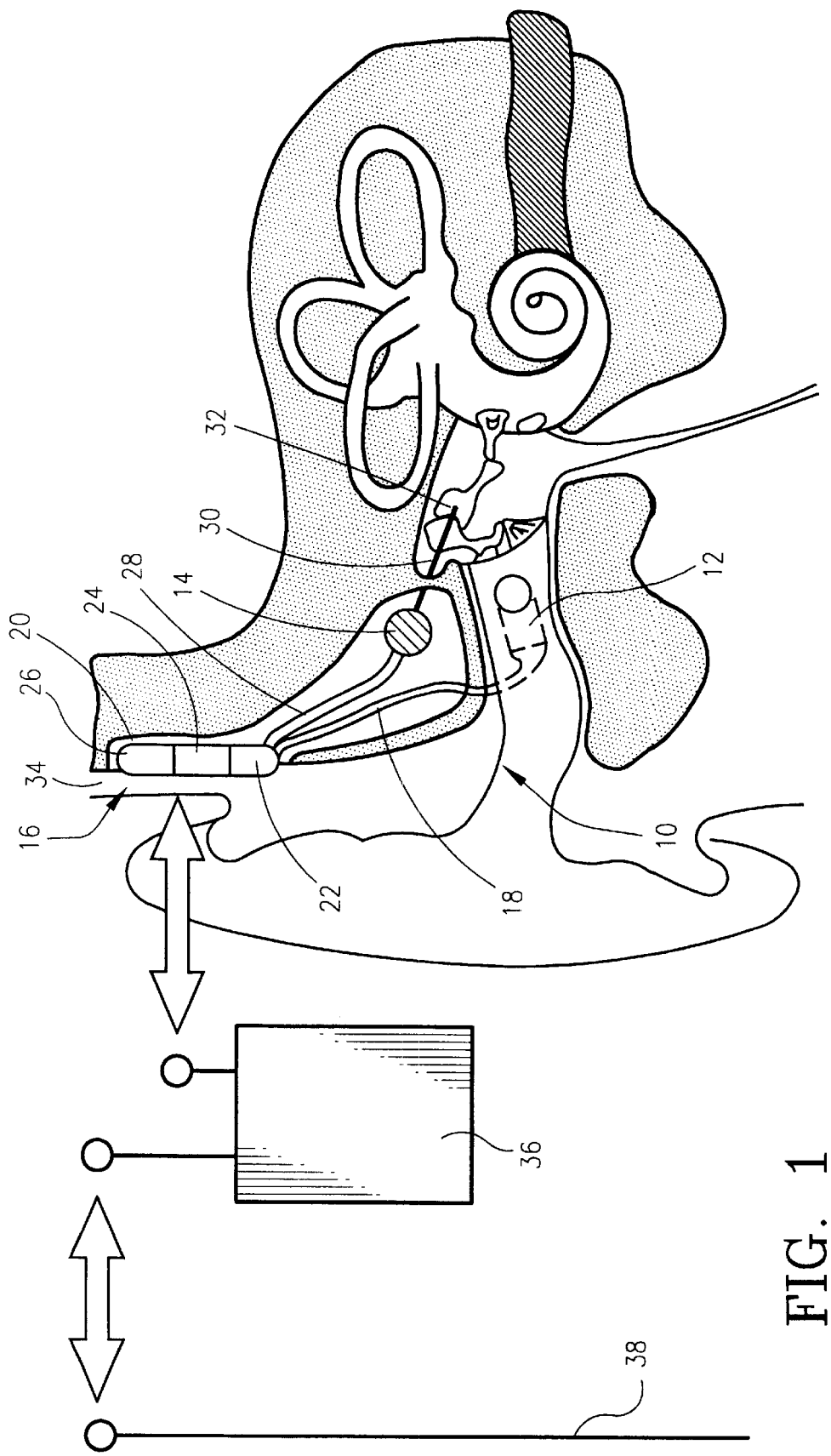
FIG. 1 schematically shows a partial sectional view of a hearing system of the invention in interaction with a telecommunication network.

FIG. 1 is a partial sectional view of a fully implantable hearing system 10 which as the major components has an acoustic pick-up 12 (microphone), an electromechanical transducer 14 and an electronic module 16. The microphone 12 which is implanted subcutaneously in the rear part of the wall of the auditory canal picks up the sound and converts it into an electrical signal which is supplied via the implant line 18 to the electronic module 16. The electronic module 16 is accommodated in a hermetically tight and biocompatible implant housing 20 which is implanted in an artificial bone bed in the mastoid area of the skull and encompasses a signal processing/control unit 22, a rechargeable electrical energy storage 24, and an RF transmitter/receiver 26. The signal processing/control unit 22, an example of which is described in the initially mentioned U.S. patent application Ser. No. 09/369,182, is used to control the operation of the hearing system and to process the electrical signals produced by the microphone 12 such that they can be supplied via an implantable line 28 to the electromechanical transducer 14 as input signals. The output side mechanical vibrations of the transducer 14 are transmitted via a suitable coupling element 30 directly to an ossicle of the ossicular chain, in this case to the incus 32. The transducer vibrations coupled to this ossicle are transmitted via the ossicular chain to the inner ear and cause a corresponding hearing impression there. Suitable coupling elements are described, for example, in U.S. Pat. No. 5,941,814, while advantageous transducers are described, among others, in U.S. Pat. No. 5,277,694, in commonly owned U.S. Pat. Nos. 6,123,660, 6,162,169, and in commonly owned co-pending U.S. patent application Ser. No. 09/465,390 which all are hereby incorporated by reference. A suitable microphone 12 is described in commonly owned U.S. Pat. No. 5,814,095 which likewise hereby is incorporated by reference.

The energy storage 24 is preferably made rechargeable, and the charging can take place, preferably inductively, in interaction with an external wireless charging unit via an energy receiving circuit (not shown) in order to provide recharging energy to the implant side, as is described for example in commonly owned U.S. Pat. No. 6,154,677 which is hereby incorporated by reference.

Aside from the RF transmitter/receiver 26, the components of the hearing system described so far are known per se. The RF transmitter/receiver 26 is designed to bidirectionally communicate through the closed skin 34 with an RF interface 36 which is positioned in local vicinity. The maximum distance to the hearing system 10 can be roughly 300 meters, as in wireless home telephones. The stationary repeater 36 which is necessary due to the limited transmission power of the RF transmitter/receiver 26 is supplied with power from the mains and is in bidirectional communication with an RF data network junction point 38 (stationary long-distance RF transmitter/receiver) as is known in mobile telephone networks. The expression "long distance" here means distances up to the conventional range of RF data network junction points. "Short distance" means distances as are allowable, for example, in wireless home telephones (up to roughly 300 m).

For an incoming call, for example, the speech signal is transmitted from the long-distance transmitter 38 to the stationary short-distance repeater 36 and from the latter through the skin to the implanted RF transmitter/receiver 26 where it is received, demodulated and fed as a (low frequency) audio signal into the audio signal path of the hearing system 10 so that this signal, which is for example the voice of the other party on the telephone, becomes audible on the implant side. The implant microphone 12 which is implanted, for example, subcutaneously in the deep bony auditory canal picks up the voice/speech of the hearing system user, converts it into an electrical signal and supplies it to the electronic module 16. Here the microphone signal is modulated onto an RF carrier and radioed from the transmitter/receiver 26 through the skin 34 to the repeater 36 which relays it to the stationary long-distance transmitter/receiver 38. The implant-side RF transmitter/receiver 26 is supplied from the same power source as the other implant components, i.e. by a primary battery or a rechargeable battery. In the fully implantable approach as shown in FIG. 1, a system which is to be worn externally on the body and which is thus visible is not required.

Dialing into the telecommunication network and control of other telecommunication functions can take place, for example, by means of voice input. In this case, the hearing system 10 must be equipped with an implant-side speech recognition module (not shown in FIG. 1) which then preferably is integrated into the electronic module 16.

Furthermore, the hearing system can have a memory for electronic buffering of the contents of the telecommunications (not shown in FIG. 1).

Figure 2:
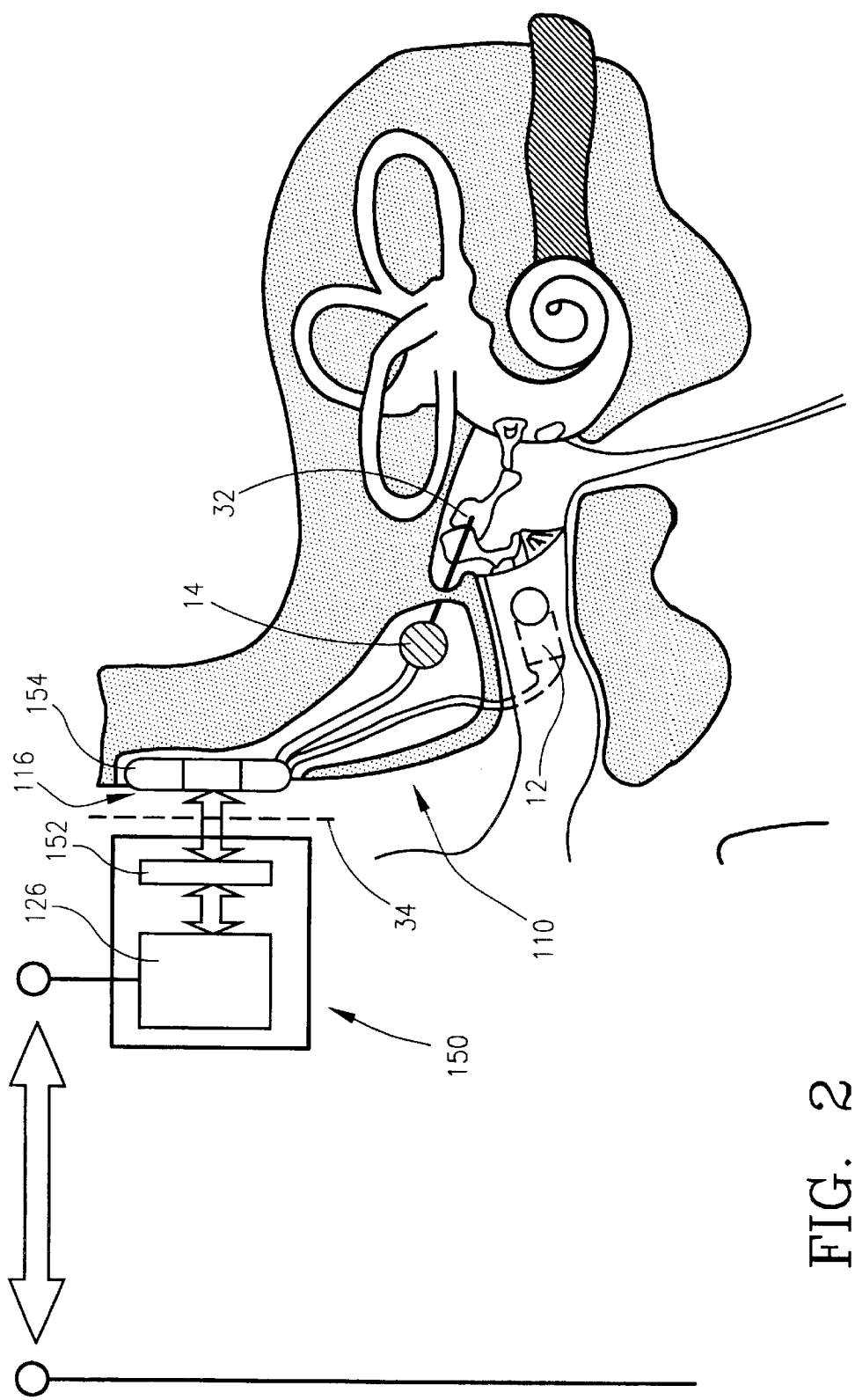
FIG. 2 shows an alternative embodiment of the linkage of the hearing system to telecommunication networks.

FIG. 2 shows an alternative embodiment of the linkage of the hearing system of FIG. 1 to telecommunication networks. The major difference is that the coupling to the RF route takes place not via an implanted RF transmitter/receiver 26, but via a transmission unit 150 which is worn on the head and which comprises, on the one hand, an RF transmitter/receiver 126 and, on the other hand, a bidirectional telemetry interface 152. In this embodiment, the implant-side RF transmitter/receiver 26 is replaced by a bidirectional wireless telemetry data interface 154 which is designed for bidirectional data exchange with the telemetry interface 152 of the transmission unit 150 which is worn on the head. The wireless telemetry between the implant and the transmission unit 150 can, in principle, also be based on an RF route, however, advantageously, an inductive transmission process is chosen. The implant-side telemetry interface 154 is formed, for example, by the charging coil for the implant-side energy storage 24 and/or by a remote control data receiving coil which can be present anyway in the implant. Other possibilities are transcutaneous infrared or ultrasonic routes.

The transmission unit 150 can be designed, for example, similar to a wireless earphone as is known, for example, in hearing support for television and can be operated by a primary or secondary cell. The RF transmitter/receiver 126 is in bidirectional data communication with the RF data network junction point, i.e. with a stationary long-distance RF transmitter/receiver 38 in the same way as the short-distance repeater 36 in the embodiment shown in FIG. 1.

The advantage of the embodiment shown in FIG. 2 is the lower power consumption of the hearing system as a result of the fact that an implant-side RF transmitter/receiver is not required. As a result of direct communication with the data network junction point 38, the transmission unit 150 acts as a mobile repeater and, in this respect, assumes the function of the stationary repeater 36 in the embodiment of FIG. 1.

Figure 3:
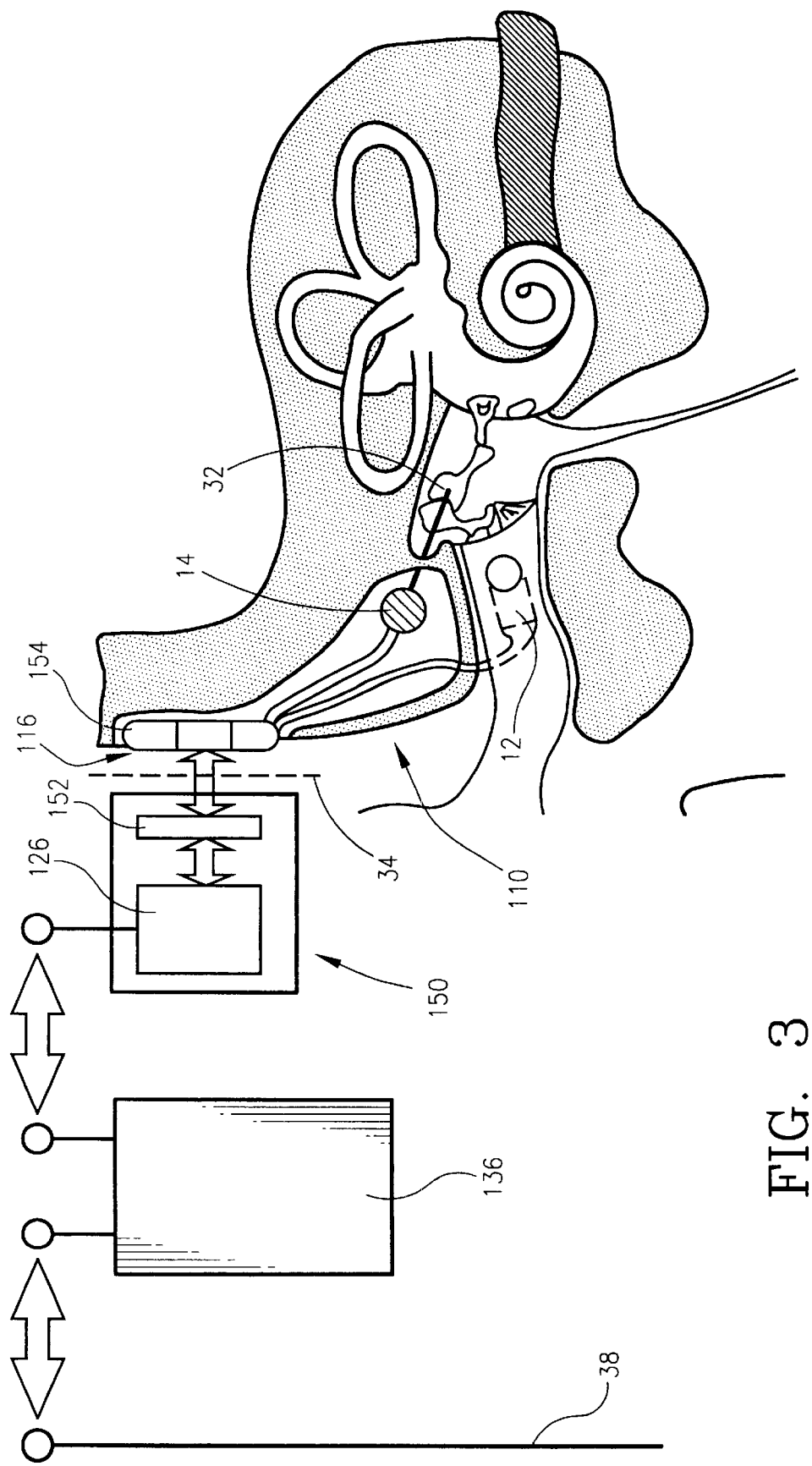
FIG. 3 shows a modification of the embodiment with a transmission unit which is worn on the head.

FIG. 3 shows a modification of the embodiment of FIG. 2 with a transmission unit 150 which is worn on the head. Here, the transmission unit 150 does not communicate directly with the telecommunication data network junction point 38, but instead via a stationary repeater 136 which provides for the actual RF coupling to the telecommunication network. In this case, the transmission unit 150 which is worn on the head does not act as a repeater, but as a wireless telemetry interface between the implant and the stationary repeater 136. In this case, the wireless data connection between the short-distance repeater 136 and the transmitter/receiver 126 of the transmission unit 150 can take place via an RF or infrared route, i.e. the transmitter/receiver unit 126 can be an RF system or an infrared system. The other system components, especially the bidirectional telemetry link between the transmission unit 150 and the implant, can be designed similar to FIG. 2.

Figure 4:
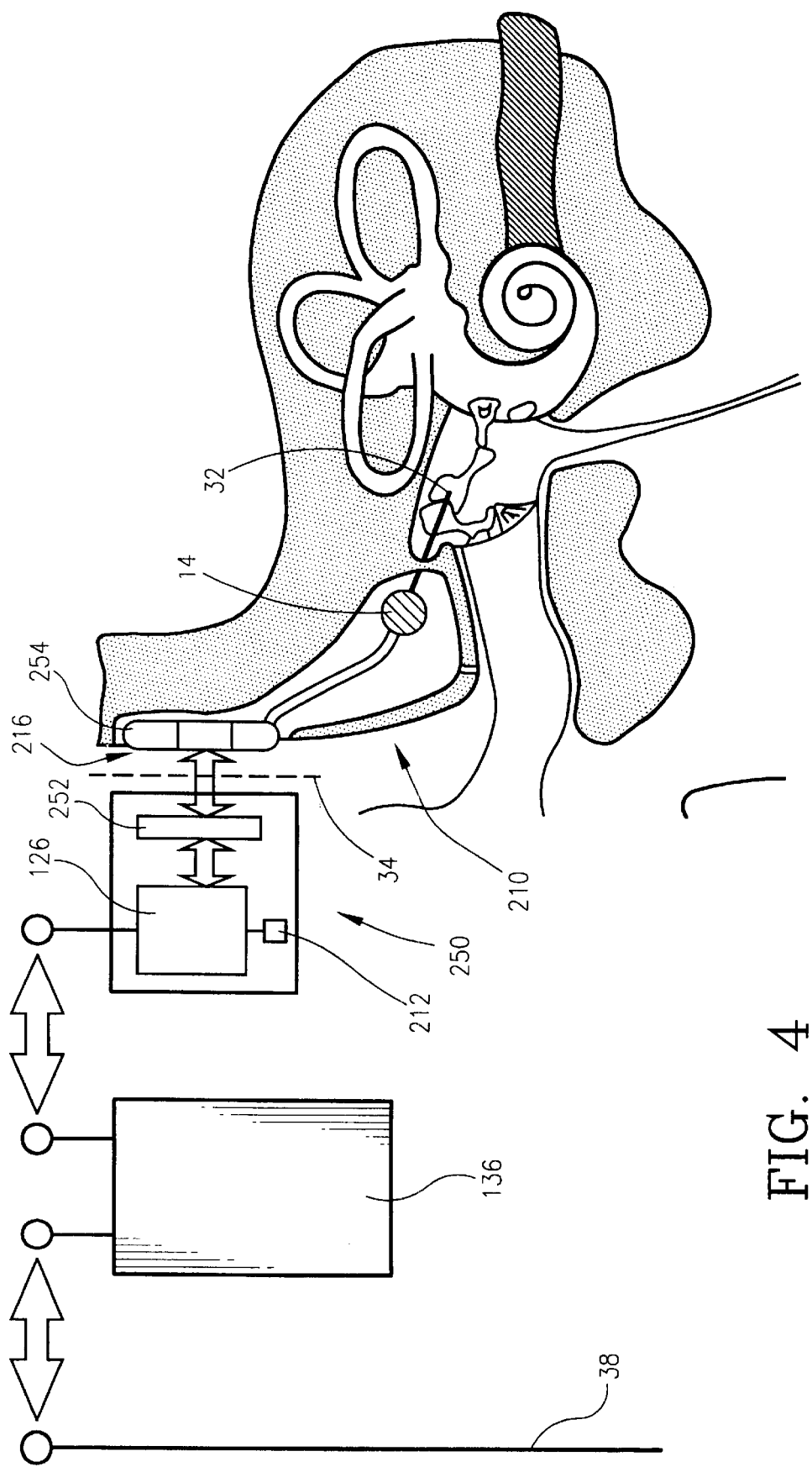
FIG. 4 shows a partially implantable system in which the acoustic pick-up microphone and the major part of the signal processing/control electronics are housed in the external transmission unit.

In the embodiment shown in FIG. 4, the linkage of the hearing system to the telecommunication network is done in the same way as in FIG. 3, i.e. a transmission unit 250 which is worn on the head contains a transmitter/receiver 126 which is in bidirectional communication with a stationary short-distance repeater 136 which in turn is in bidirectional communication via an RF route with the telecommunication network junction point 38. In contrast to the embodiments as shown in FIGS. 1 to 3, however, the hearing system 210 is not made as a fully implantable system, but as a partially implantable system in which the acoustic pick-up microphone 212 and preferably the major part of the signal processing/control electronics are housed in the external transmission unit 250. The implant-side electronic module 216 can be made passive in terms of energy, and, like ordinary partial implants, the operating energy and the signal data can be transcutaneously received and demodulated, there then being no implant-side energy storage 24. However, the implant, as in the preceding embodiments, alternatively can contain an active power supply in the form of a primary battery or rechargeable battery. Another difference from the embodiment shown in FIG. 3 is that the transcutaneous data link between the external telemetry interface 252 and the implant-side telemetry interface 254 can be unidirectional only from the transmission unit 250 to the implant-side electronic module 216 since the latter does not produce a picked-up acoustic signal.

Figure 5:
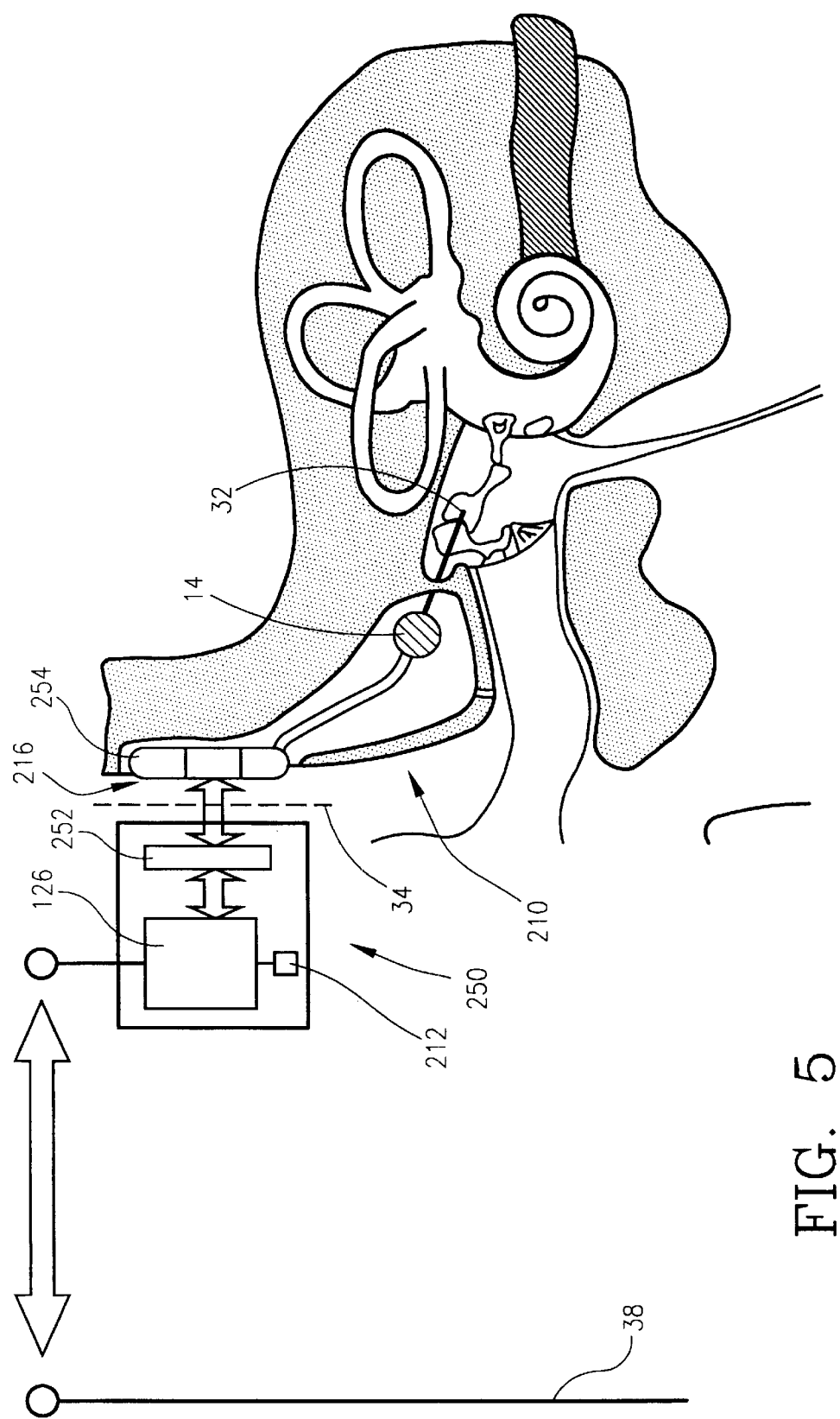
FIG. 5 shows an embodiment in which the stationary short-distance repeater is abandoned and the transmitter/receiver unit of the transmission unit which is worn on the head is designed as an RF transmitter/receiver for direct bidirectional communication with the long-distance telecommunication network junction point and acts in this respect as an RF repeater.

FIG. 5 shows an embodiment which differs from the embodiment shown in FIG. 4 essentially in that, as in the embodiment shown in FIG. 2, the stationary short-distance repeater is abandoned and the transmitter/receiver unit 126 of the transmission unit 250 which is worn on the head is designed as an RF transmitter/receiver for direct bidirectional communication with the long-distance telecommunication network junction point 38 and acts in this respect as an RF repeater.

Figure 6:
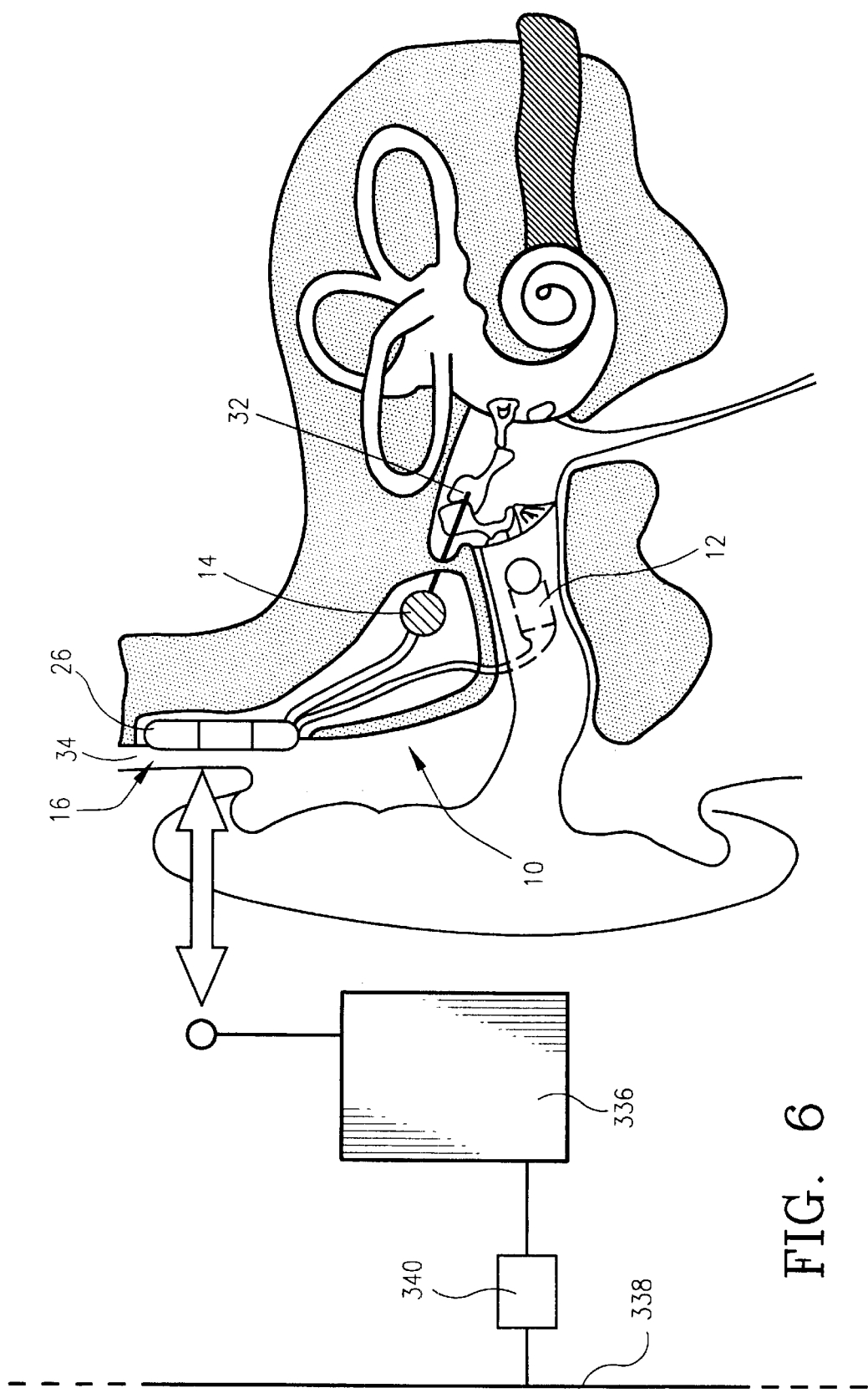
FIG. 6 shows a modification where the stationary short-distance RF transmitter/receiver or repeater implements a wire coupling to a wire-linked telecommunication network.

FIG. 6 shows a modification of the embodiment shown in FIG. 1, the stationary short-distance RF transmitter/receiver or repeater not being made for coupling to a telecommunication network via a wireless RF route, but instead implements a wire coupling to a wire-linked telecommunication network 338. As in FIG. 1, the repeater 336 is in bidirectional wireless RF communication with the implant 10. The wire-linked coupling to the telecommunication network 338 takes place optionally via an adapter 340 which provides for the respective conversion to the hardware design of the telecommunication network (cable, optical fiber, power supply network, etc.).

The concept shown in FIG. 6 can, of course, also be used for all other embodiments in which there is a stationary short-distance repeater.

Figure 7:
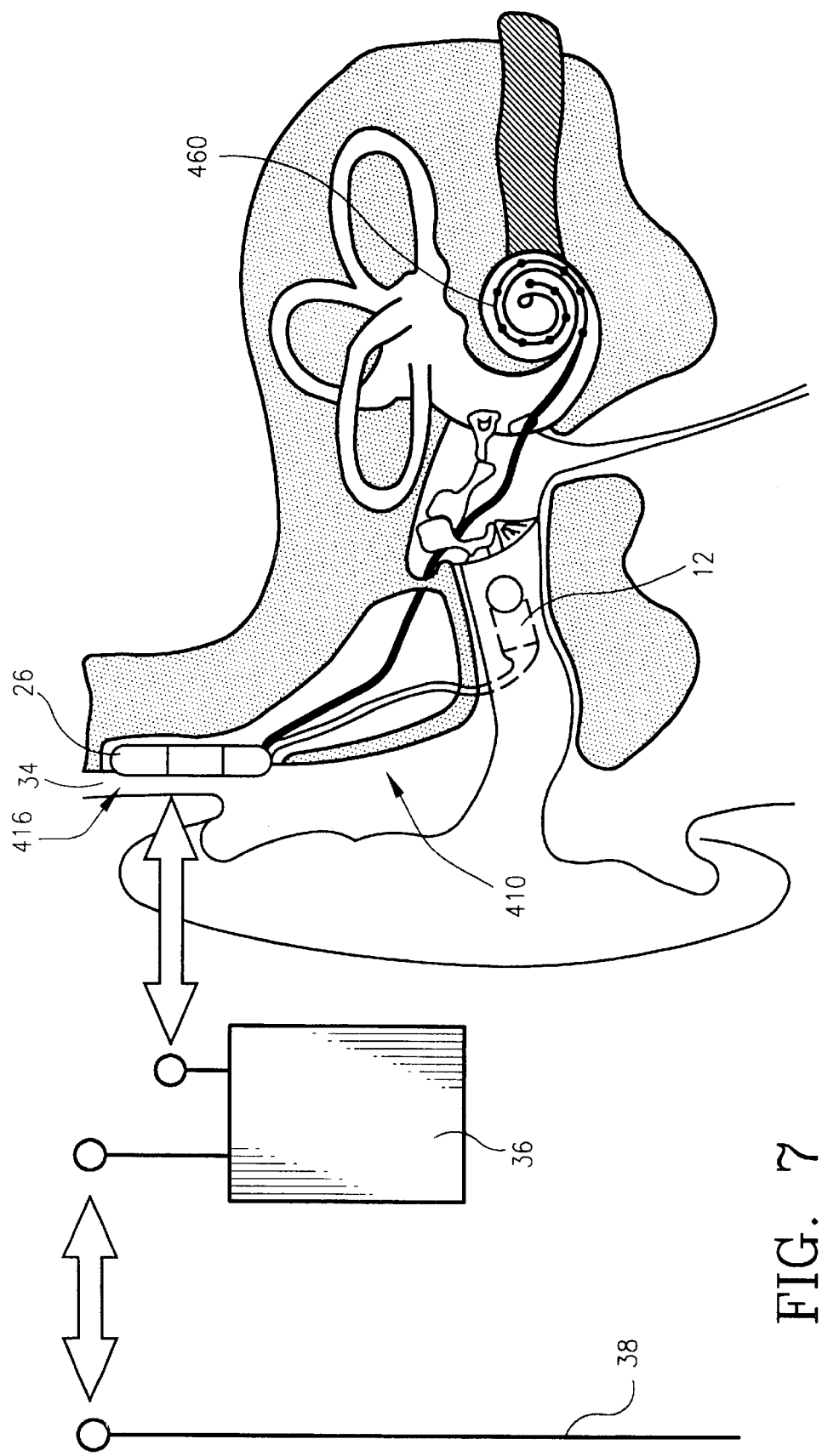
FIG. 7 shows a fully implantable hearing system which includes a unit for electrical stimulation of the inner ear.

FIG. 7 shows a fully implantable hearing system 410 which, instead of an electromechanical transducer for mechanical stimulation of the ossicular chain or for direct mechanical stimulation of the inner ear, includes a unit for electrical stimulation of the inner ear, which is an intercochlear multielectrode array 460 which is known per se and which can be designed in the conventional manner. With respect to linkage to the telecommunication network, FIG. 7 shows the linkage concept as shown in FIG. 1, in which the implant electronic module 416 comprises an RF transmitter/receiver 26 for bidirectional communication with a stationary short-distance RF repeater 36 which, in turn, is in bidirectional communication with a long-distance telecommunication junction point 38.

The embodiments described so far were related to hearing systems for bidirectional linkage to a telecommunication network, the hearing system basically assuming all functions of a telecommunication terminal device, for example, a mobile phone.

Figure 8:
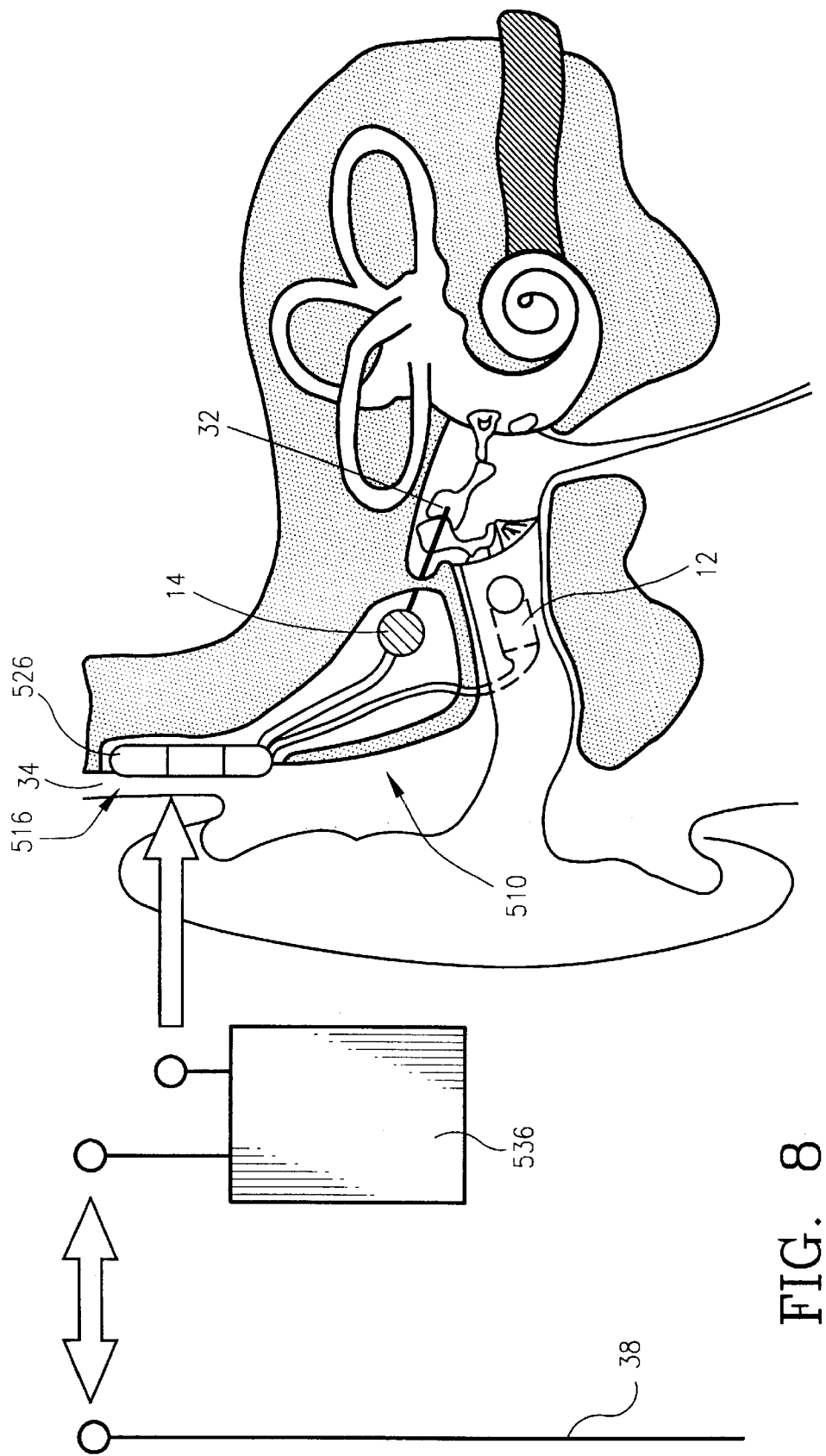
FIG. 8 shows an embodiment for hearing systems which allows only implant-side reception of speech-based messages from the telecommunication network.
Figure 9:
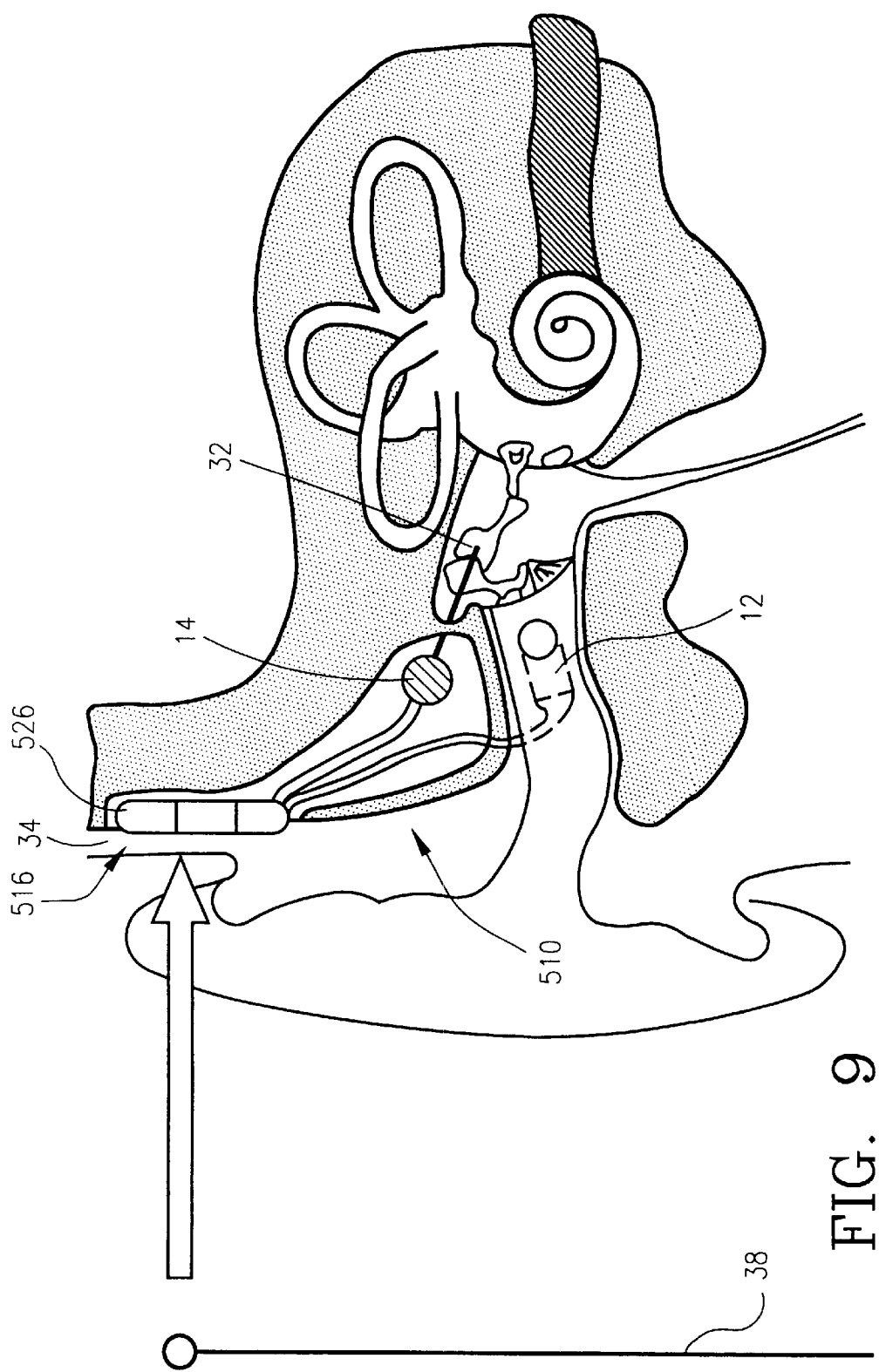
FIG. 9 shows an embodiment where data are transmitted purely unidirectionally from a stationary long-distance RF transmitter/receiver (telecommunication network junction point) directly to the implant-side RF receiver.

FIGS. 8 and 9 show embodiments for hearing systems which allow only implant-side reception of speech-based messages from the telecommunication network. The embodiment shown in FIG. 8 differs from the embodiment shown in FIG. 1 essentially only in that, instead of an RF transmitter/receiver, there is provided in the electronic module 516 only an RF receiver 526 which receives signals from a stationary short-distance repeater 536 which is in bidirectional communication with a stationary long-distance RF transmitter/receiver 38 which forms a telecommunication network junction point. The telecommunication signal received from the RF receiver 526 is demodulated by the latter and, as in the preceding embodiments, the speech information obtained in this way is fed to the audio signal path of the implanted hearing system 510. The stationary short-distance RF transmitter/receiver 536 is in bidirectional communication with the junction point 38 to signal its readiness for reception and, for example, to transmit reception acknowledgments to the telecommunication network.

The embodiment shown in FIG. 9 differs from the embodiment shown in FIG. 8 essentially in that a stationary RF transmitter/receiver as an external intermediate station is omitted and the data are transmitted purely unidirectionally from a stationary long-distance RF transmitter/receiver 38 (telecommunication network junction point) directly to the implant-side RF receiver 526. Since there is no data return path here, in this case, readiness for reception or reception acknowledgment cannot be signaled.

The hearing systems described above in conjunction with bidirectional linkage to the telecommunication network basically can also be designed for a unidirectional link to the telecommunication network, i.e. one which allows only reception.

Figure 10:
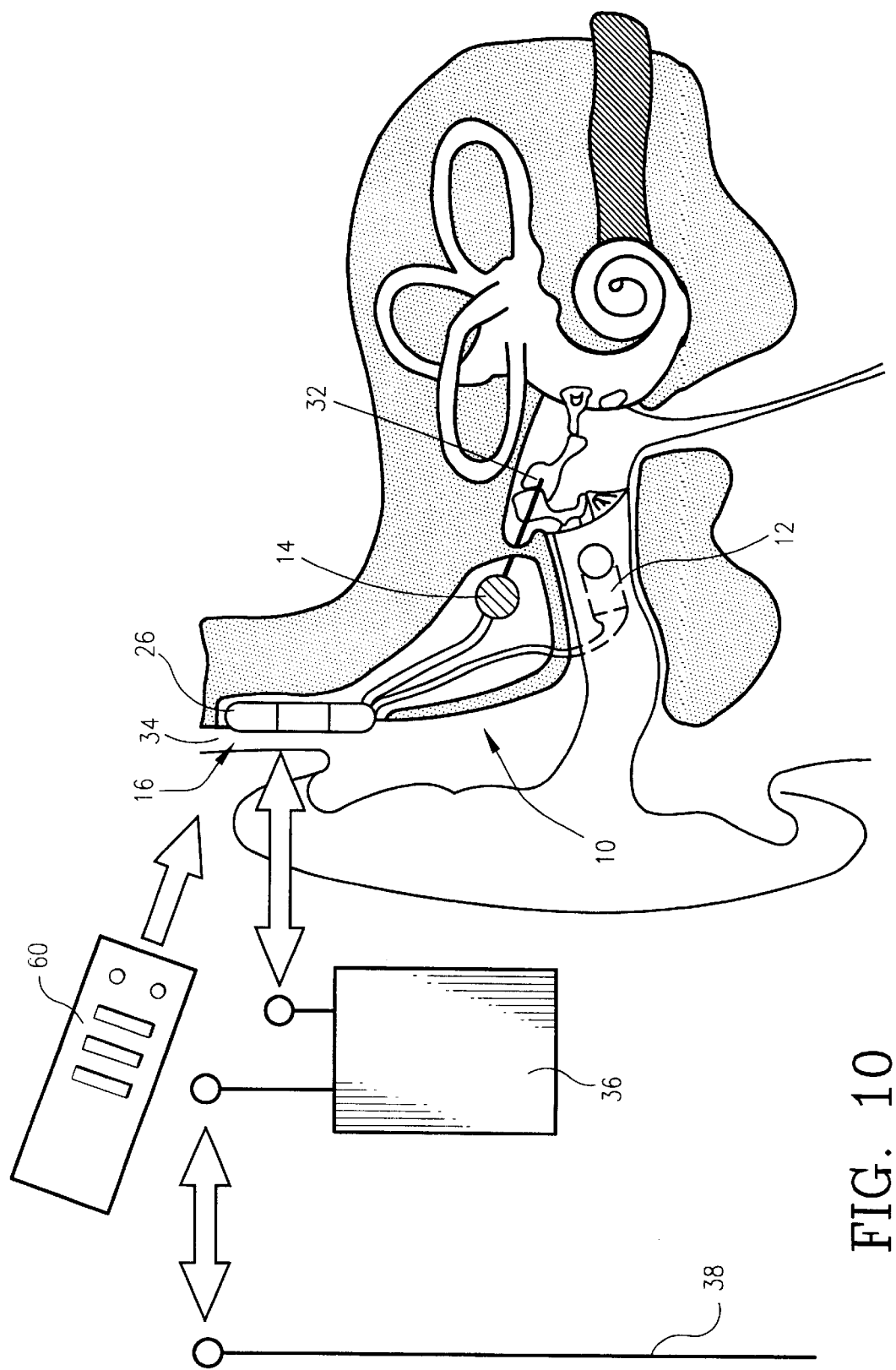
FIG. 10 shows a modification of the embodiment of FIG. 1 comprising a wireless remote control.

FIG. 10 shows a modification of the embodiment shown in FIG. 1, in which, in addition, there is a wireless remote control 60 for control of telecommunication functions of the implant 10, for example, dialing into the network, adjustment of the volume of reception, etc. Communication takes place unidirectionally from the remote control 60 to the electronic module 16. Here, for example, communication can take place by means of an RF route via the RF transmitter/receiver 26 of the implant 10 which is present anyway. Alternatively, however, communication can also take place via an inductive route or an infrared or ultrasonic route. When inductive transmission is selected, for example, a charging coil and/or a receiving coil can be used which is/are already present in the implant anyway in order to enable data exchange with respect to the actual hearing system functions, for example, parameter adjustment or software updating, as is described, for example, in commonly owned, co-pending U.S. patent application Ser. No. 09/369,182 which is hereby incorporated by reference.

If the implant contains a storage for electronic buffering of telecommunication messages, the remote control 60 can also be used to retrieve such buffered messages.

Such a remote control basically can also be used for control of implant-side telecommunication functions in all other embodiments of the invention described above. The partially or fully implantable hearing system can also be a binaural system, as is explained, for example, with reference to FIG. 5 of the aforementioned U.S. patent application Ser. No. 09/369,182.

Figure 11:
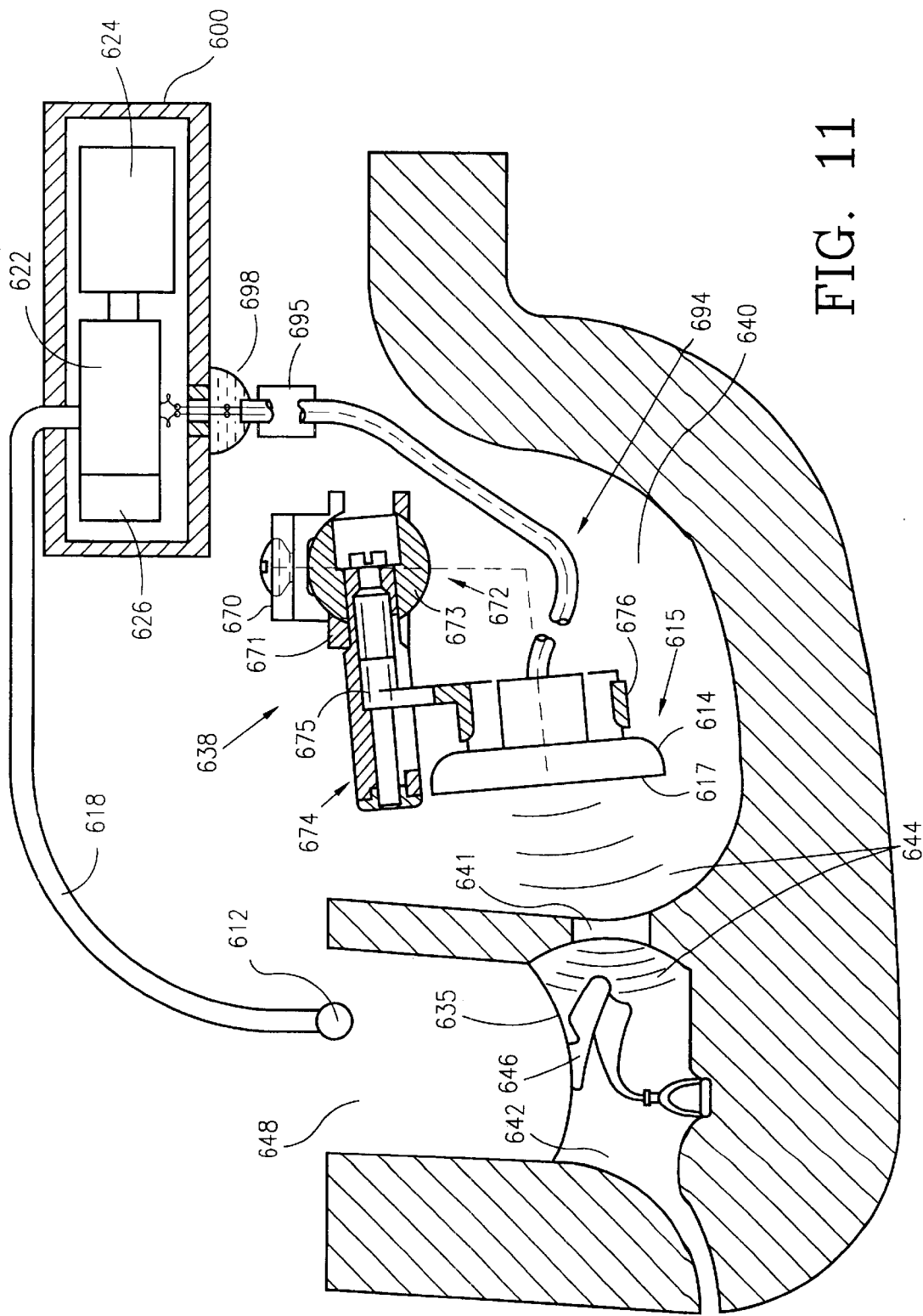
FIG. 11 shows a hearing system wherein the electromechanical transducer is a replaced by an electroacoustic transducer.

FIG. 11 illustrates an embodiment of a fully implantable system wherein the electromechanical transducer is replaced by an electroacoustic transducer 615. The transducer 615 is held with its housing 614 in an implantable positioning and fixing system 638, as is described for example in published European patent application no. 0 812 577. This positioning and fixing system is used to align and permanently fix the transducer 615, based on the given individual anatomic circumstance in the artificial mastoid cavity, such that the sound-emitting transducer membrane 617 is as near the aditus ad antrum 641 as possible. The transducer 615 sits in the implanted state in an artificial mastoid cavity 640 which is openly connected, via the aditus ad antrum 641, to the tympanic cavity 642. During operation, the membrane 617 of the transducer 615, positioned opposite the aditus ad antrum 641, emits sound waves 644 which pass into the tympanic cavity 642 causing the eardrum 635 to vibrate mechanically. Depending on the existing individual anatomical aspects, it may be necessary to surgically slightly widen the aditus ad antrum 641 during implantation after completed (partial) mastoidectomy in order to ensure reliable passage of sound from the mastoid cavity 640 into the tympanic cavity 642. Mechanical vibrations travel via mechanical transmission through the middle ear ossicle chain 646 to the inner ear causing an auditory impression via direct acoustic excitation of the oval or round window of the inner ear. In FIG. 11, the outer auditory canal is indicated at 648.

The positioning and fixing system 638 includes a head plate 670 suitable for bone anchoring and a ball joint 672 fixed by a clamping mechanism 671 manually positioned using an auxiliary tool and attached to the head plate 670. The system 638 further includes a linear drive arrangement 674 which is permanently connected to the ball 673 of the ball joint 672, a carriage 675 guided along a guide of the linear drive arrangement 674 and a receiver 676 attached to the carriage 675 for the transducer housing 614. The carriage can be freely positioned manually along the guide via a drive. The transducer 615 is connected by means of an implantable electric lead wire 694 to an implantable, hermetically tightly sealed implant housing 600 via a signal feed-through 698.

The implant housing 600 is configured such that it can be placed in an artificial bone bed on the mastoid plane behind the pertinent outer ear. The housing 600 contains an RF transmitter/receiver 626 for connecting the hearing system to telecommunication networks, a signal processing/control unit 622 and rechargeable electrical energy storage 624. A microphone 612 which is implanted in the wall of the auditory canal 648 is electrically connected to the signal processing/control unit 622 via an implant line 618. Alternatively, an external microphone like in the embodiment of FIG. 4 may be provided.

Advantageously, the electrical converter lead wire 694 is not permanently connected to the housing 600, but via a detachable connector 695 which satisfies the corresponding implant requirement with respect to electrical insulation and tightness.

The housing 600 and the units contained therein are similar to the embodiments according to FIGS. 1 to 10. In particular, the RF transmitter/receiver 626, may be provided for bidirectional or unidirectional communication according to any of the embodiments of FIGS. 1 to 10.

While several embodiments in accordance with the present invention has been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

We claim:

1. Implantable hearing system comprising a stimulation unit for stimulation of one of a middle ear and an inner ear wherein the hearing system comprises linkage means for direct linkage of the unit to telecommunication networks without using telecommunication terminal devices.

2. Hearing system as claimed in claim 1, wherein the stimulation unit is provided with an acoustic pick-up.

3. Hearing system as claimed in claim 2, wherein the linkage means is bidirectional.

4. Hearing system as claimed in claim 3, wherein the linkage means comprises transmission/reception means for wireless transmission and reception of signals.

5. Hearing system as claimed in claim 4, wherein the transmission/reception means comprises a headwearable transmission unit which has an acoustic pick-up, a transmission-reception means and a transmission means for unidirectional communication via an implanted receiver with implantable components of the hearing system.

6. Hearing system as claimed in claim 5, wherein the transmission means comprises one of an inductive, a transcutaneous infrared, and a transcutaneous ultrasonic means for communication between the transmission means and the implanted receiver.

7. Hearing system as claimed in claim 4, wherein the transmission-reception means comprises an RF transmitter/receiver means.

8. Hearing system as claimed in claim 7, wherein the RF transmitter/receiver means is provided with a stationary repeater unit.

9. Hearing system as claimed in claim 8, wherein the stationary repeater unit is communicatable with an RF telecommunication network junction point.

10. Hearing system as claimed in claim 8, wherein the stationary repeater unit is connected to a wire-linked telecommunication network by a wired coupling.

11. Hearing system as claimed in claim 7, wherein the RF transmitter/receiver means is communicatable with an RF telecommunication network junction point.

12. Hearing system as claimed in claim 4, wherein the transmission/reception means is operable for communicating with a heat wearable transmission unit.

13. Hearing system as claimed in claim 12, wherein said transmission/reception means is constructed for one of inductive transcutaneious infrared and ultrasonic transmission and reception.

14. Hearing system according to claim 13, wherein the transmission/reception means comprise one of a receiving coil for the energy storage and a remote data exchange receiving coil.

15. Hearing system as claimed in claim 12, wherein the transmission unit is communicatable with an RF telecommunication network junction point.

16. Hearing system as claimed in claim 12, wherein the headwearable transmission unit is communicatable with a stationary repeater unit.

17. Hearing system as claimed in claim 4, wherein the transmission-reception means is implantable.

18. Hearing system as claimed in claim 17, wherein the stimulation unit includes an electronic module to produce an input signal from the signal acquired by a acoustic pick-up for stimulation of one of the middle ear and the inner ear.

19. Hearing system as claimed in claim 18, wherein the electronic module comprises a wirelessly chargeable storage for electrical energy.

20. Hearing system as claimed in claim 18, wherein the transmission/reception means is integrated into the electronic module.

21. Hearing system as claimed in claim 17, wherein the entire hearing system is implantable.

22. Hearing system as claimed in claim 21, wherein the acoustic pick-up is an implantable microphone for picking up sound in a auditory canal of a person in which the system is implanted in use.

23. Hearing system as claimed in claim 1, wherein the linkage means is unidirectional from the telecommunication network to the hearing system.

24. Hearing system as claimed in claim 23, wherein the linkage means includes means for wireless reception of signals.

25. Hearing system as claimed in claim 24, wherein the receiving means comprises an RF receiver means.

26. Hearing system as claimed in claim 25, further comprising a stationary repeater unit for transmission of RF signals to the RF receiver means.

27. Hearing system as claimed in claim 26, wherein the stationary repeater unit is bidirectional and communicates with an RF telecommunication network junction point.

28. Hearing system as claimed in claim 25, wherein the RF receiver means is operable for receiving RF signals from an RF telecommunication network junction point.

29. Hearing system as claimed in claim 1, wherein the stimulation unit comprises an electromechanical transducer and a rigid coupling element driven by the transducer and which in use, is coupled to one of a middle ear ossicle and an oval window.

30. Hearing system as claimed in claim 1, wherein the stimulation unit comprises a plurality of electrodes are implantable into the cochlea.

31. Hearing system as claimed in claim 1, wherein the hearing system comprises a storage for electronic buffering of the contents of telecommunications.

32. Hearing system as claimed in claim 1, wherein the hearing system comprises a speech recognition module for speech-controlled dialing into the telecommunication network.

33. Hearing system as claimed in claim 1, wherein the hearing system is designed for communicatable with a wireless remote control for control of one of dialing into the telecommunication network, retrieval of buffered messages, and volume adjustment of voice messages of the hearing system.

34. Hearing system as claimed in claim 1, wherein the hearing system is operable for rehabilitation of a hearing disorder of one of the middle ear and the inner ear of a user.

35. Hearing system as claimed in claim 1, wherein the hearing system is operable for a user without a hearing disorder.

36. Hearing system as claimed in claim 1, wherein the stimulation unit comprises an electroacoustic transducer.

* * * * *